United States Patent
Rioux et al.

(10) Patent No.: US 10,869,714 B2
(45) Date of Patent: Dec. 22, 2020

(54) RESECTING AND COAGULATING TISSUE

(71) Applicant: Innoblative Designs, Inc., Chicago, IL (US)

(72) Inventors: Robert F. Rioux, Ashland, MA (US); Tyler Wanke, Chicago, IL (US); Ryan M. Bean, Westminster, MA (US); Michelle Hasse, Eau Claire, MI (US)

(73) Assignee: Innoblative Designs, Inc., Chicago, IL (US)

( * ) Notice: Subject to any disclaimer, the term of this patent is extended or adjusted under 35 U.S.C. 154(b) by 47 days.

(21) Appl. No.: 15/442,079

(22) Filed: Feb. 24, 2017

(65) Prior Publication Data

US 2017/0252092 A1    Sep. 7, 2017

Related U.S. Application Data

(60) Provisional application No. 62/301,907, filed on Mar. 1, 2016.

(51) Int. Cl.
*A61B 18/14* (2006.01)
*A61B 18/00* (2006.01)
*A61B 18/12* (2006.01)

(52) U.S. Cl.
CPC .. *A61B 18/1402* (2013.01); *A61B 2018/0016* (2013.01); *A61B 2018/00029* (2013.01);
(Continued)

(58) Field of Classification Search
CPC ...... A61B 2018/0016; A61B 2018/144; A61B 2018/1467; A61B 2018/00589; A61B 2018/00601; A61B 2018/00607; A61B 2018/00654; A61B 18/14; A61B 18/1402; A61B 2018/00029; A61B 2018/00083; A61B 2018/00529; A61B 2018/00577;
(Continued)

(56) References Cited

U.S. PATENT DOCUMENTS 4,699,147 A   10/1987   Chilson et al.
4,976,711 A   12/1990   Parins et al.
(Continued)

FOREIGN PATENT DOCUMENTS

CN   2610858 Y      4/2004
CN   104546124 A    4/2015
(Continued)

OTHER PUBLICATIONS

International Search Report and Written Opinion of the International Searching Authority dated Oct. 19, 2017 for International Application No. PCT/US2017/041501 (63 Pages).
(Continued)

*Primary Examiner* — Eun Hwa Kim
*Assistant Examiner* — Adam Z Minchella
(74) *Attorney, Agent, or Firm* — Brown Rudnick LLP

(57) ABSTRACT

The invention generally relates to a tissue ablation system including an ablation device to be delivered to a target site and achieve both resection and coagulation of tissue. The ablation device can be used during an electrosurgical resection procedure to both resect tissue and further selectively coagulate surrounding tissue in the resection site so as to prevent or stop fluid accumulation (e.g., blood from vessel (s)) as a result of the resection of tissue.

16 Claims, 5 Drawing Sheets

(52) U.S. Cl.
CPC ......... *A61B 2018/0063* (2013.01); *A61B 2018/0072* (2013.01); *A61B 2018/00083* (2013.01); *A61B 2018/00529* (2013.01); *A61B 2018/00577* (2013.01); *A61B 2018/00589* (2013.01); *A61B 2018/00601* (2013.01); *A61B 2018/00607* (2013.01); *A61B 2018/00654* (2013.01); *A61B 2018/00755* (2013.01); *A61B 2018/00767* (2013.01); *A61B 2018/00875* (2013.01); *A61B 2018/00958* (2013.01); *A61B 2018/124* (2013.01); *A61B 2018/126* (2013.01); *A61B 2018/1253* (2013.01); *A61B 2018/144* (2013.01); *A61B 2018/1467* (2013.01); *A61B 2018/1472* (2013.01); *A61B 2218/002* (2013.01)

(58) Field of Classification Search
CPC .... A61B 2018/0063; A61B 2018/0072; A61B 2018/00755; A61B 2018/00767; A61B 2018/00875; A61B 2018/00958; A61B 2018/124; A61B 2018/1253; A61B 2018/126; A61B 2018/1472; A61B 2218/002
See application file for complete search history.

(56) References Cited

U.S. PATENT DOCUMENTS

| | | | |
|---|---|---|---|
| 4,979,948 A | 12/1990 | Geddes et al. | |
| 5,045,056 A | 9/1991 | Behl | |
| 5,100,423 A | 3/1992 | Fearnot | |
| 5,117,828 A | 6/1992 | Metzger et al. | |
| 5,163,938 A * | 11/1992 | Kambara | A61B 18/14 606/47 |
| 5,334,193 A | 8/1994 | Nardella | |
| 5,429,605 A | 7/1995 | Richling et al. | |
| 5,471,982 A | 12/1995 | Edwards et al. | |
| 5,472,441 A | 12/1995 | Edwards et al. | |
| 5,486,161 A | 1/1996 | Lax et al. | |
| 5,536,267 A | 7/1996 | Edwards et al. | |
| 5,562,720 A | 10/1996 | Stern et al. | |
| 5,657,760 A | 8/1997 | Ying et al. | |
| 5,672,153 A | 9/1997 | Lax et al. | |
| 5,672,173 A | 9/1997 | Gough et al. | |
| 5,672,174 A | 9/1997 | Gough et al. | |
| 5,683,384 A | 11/1997 | Gough et al. | |
| 5,713,942 A | 2/1998 | Stern et al. | |
| 5,728,143 A | 3/1998 | Gough et al. | |
| 5,772,590 A | 6/1998 | Webster, Jr. | |
| 5,782,827 A | 7/1998 | Gough et al. | |
| 5,827,276 A | 10/1998 | LeVeen et al. | |
| 5,840,076 A | 11/1998 | Swanson et al. | |
| 5,846,239 A | 12/1998 | Swanson et al. | |
| 5,855,576 A | 1/1999 | LeVeen et al. | |
| 5,863,290 A | 1/1999 | Gough et al. | |
| 5,868,736 A | 2/1999 | Swanson et al. | |
| 5,868,776 A | 2/1999 | Wright | |
| 5,871,483 A | 2/1999 | Jackson et al. | |
| 5,888,198 A | 3/1999 | Eggers et al. | |
| 5,891,136 A | 4/1999 | McGee et al. | |
| 5,893,847 A | 4/1999 | Kordis | |
| 5,913,855 A | 6/1999 | Gough et al. | |
| 5,928,229 A | 7/1999 | Gough et al. | |
| 5,935,123 A | 8/1999 | Edwards et al. | |
| 5,961,513 A | 10/1999 | Swanson et al. | |
| 5,980,517 A | 11/1999 | Gough | |
| 6,009,877 A * | 1/2000 | Edwards | A61N 1/40 128/898 |
| 6,032,077 A | 2/2000 | Pomeranz | |
| 6,036,689 A | 3/2000 | Tu et al. | |
| 6,053,913 A | 4/2000 | Tu et al. | |
| 6,053,937 A | 4/2000 | Edwards et al. | |
| 6,063,081 A | 5/2000 | Mulier et al. | |
| 6,071,278 A | 6/2000 | Panescu et al. | |
| 6,071,280 A | 6/2000 | Edwards et al. | |
| 6,099,526 A | 8/2000 | Whayne et al. | |
| 6,112,123 A | 8/2000 | Kelleher et al. | |
| 6,123,718 A | 9/2000 | Tu et al. | |
| 6,142,993 A | 11/2000 | Whayne et al. | |
| 6,221,071 B1 | 4/2001 | Sherry et al. | |
| 6,241,666 B1 | 6/2001 | Pomeranz et al. | |
| 6,251,109 B1 | 6/2001 | Hassett et al. | |
| 6,258,087 B1 | 7/2001 | Edwards et al. | |
| 6,309,352 B1 | 10/2001 | Oraevsky et al. | |
| 6,312,408 B1 * | 11/2001 | Eggers | A61B 18/12 604/114 |
| 6,312,429 B1 | 11/2001 | Burbank et al. | |
| 6,358,248 B1 | 3/2002 | Mulier et al. | |
| 6,379,353 B1 | 4/2002 | Nichols | |
| 6,409,722 B1 | 6/2002 | Hoey et al. | |
| 6,425,877 B1 | 7/2002 | Edwards | |
| 6,454,766 B1 | 9/2002 | Swanson et al. | |
| 6,491,710 B2 | 12/2002 | Satake | |
| 6,494,902 B2 | 12/2002 | Hoey et al. | |
| 6,503,247 B2 | 1/2003 | Swartz et al. | |
| 6,522,930 B1 | 2/2003 | Schaer et al. | |
| 6,537,248 B2 | 3/2003 | Mulier et al. | |
| 6,537,272 B2 | 3/2003 | Christopherson et al. | |
| 6,544,262 B2 | 4/2003 | Fleischman | |
| 6,551,310 B1 | 4/2003 | Ganz et al. | |
| 6,585,732 B2 | 7/2003 | Mulier et al. | |
| 6,623,481 B1 | 9/2003 | Garbagnati et al. | |
| 6,638,275 B1 | 10/2003 | McGaffigan et al. | |
| 6,648,883 B2 | 11/2003 | Francischelli et al. | |
| 6,663,622 B1 | 12/2003 | Foley et al. | |
| 6,692,466 B1 | 2/2004 | Chow et al. | |
| 6,736,810 B2 | 5/2004 | Hoey et al. | |
| 6,736,811 B2 | 5/2004 | Panescu et al. | |
| 6,743,226 B2 | 6/2004 | Cosman et al. | |
| 6,764,487 B2 | 7/2004 | Mulier et al. | |
| 6,770,072 B1 | 8/2004 | Truckai et al. | |
| 6,780,183 B2 | 8/2004 | Jimenez, Jr. et al. | |
| 6,805,131 B2 | 10/2004 | Kordis | |
| 6,826,421 B1 | 11/2004 | Beatty et al. | |
| 6,849,073 B2 | 2/2005 | Hoey et al. | |
| 6,872,206 B2 | 3/2005 | Edwards et al. | |
| 6,878,149 B2 | 4/2005 | Gatto | |
| 6,955,641 B2 | 10/2005 | Lubock | |
| 6,978,788 B2 | 12/2005 | Klimberg et al. | |
| 6,984,232 B2 | 1/2006 | Vanney et al. | |
| 7,104,989 B2 | 9/2006 | Skarda | |
| 7,150,745 B2 | 12/2006 | Stern et al. | |
| 7,156,845 B2 | 1/2007 | Mulier et al. | |
| 7,169,144 B2 | 1/2007 | Hoey et al. | |
| 7,247,155 B2 | 7/2007 | Hoey et al. | |
| 7,276,061 B2 | 10/2007 | Schaer et al. | |
| 7,306,593 B2 | 12/2007 | Keidar et al. | |
| 7,326,208 B2 | 2/2008 | Vanney et al. | |
| 7,344,535 B2 | 3/2008 | Stern et al. | |
| 7,364,579 B2 | 4/2008 | Mulier et al. | |
| 7,367,972 B2 | 5/2008 | Francischelli et al. | |
| 7,371,231 B2 | 5/2008 | Rioux et al. | |
| 7,399,299 B2 | 7/2008 | Daniel et al. | |
| 7,416,552 B2 | 8/2008 | Paul et al. | |
| 7,419,489 B2 | 9/2008 | Vanney et al. | |
| 7,556,628 B2 | 7/2009 | Utley et al. | |
| 7,632,268 B2 | 12/2009 | Edwards et al. | |
| 7,717,909 B2 | 5/2010 | Strul et al. | |
| 7,769,432 B2 | 8/2010 | Klimberg et al. | |
| 7,776,034 B2 | 8/2010 | Kampa | |
| 7,828,793 B2 | 11/2010 | Thompson et al. | |
| 7,862,498 B2 | 1/2011 | Nguyen et al. | |
| 7,879,030 B2 | 2/2011 | Paul et al. | |
| 7,942,873 B2 | 5/2011 | Kwan et al. | |
| 7,959,628 B2 | 6/2011 | Schaer et al. | |
| 7,959,631 B2 | 6/2011 | DiCarlo | |
| 8,034,022 B2 | 10/2011 | Boatman | |
| 8,043,289 B2 | 10/2011 | Behl et al. | |
| 8,048,069 B2 | 11/2011 | Skwarek et al. | |
| 8,114,071 B2 | 2/2012 | Woloszko et al. | |
| 8,224,416 B2 | 7/2012 | de la Rama et al. | |
| 8,303,584 B2 | 11/2012 | Burdio Pinilla et al. | |
| 8,388,573 B1 | 3/2013 | Cox | |

(56) References Cited

U.S. PATENT DOCUMENTS

| | | |
|---|---|---|
| 8,398,624 B2 | 3/2013 | Rioux et al. |
| 8,409,193 B2 | 4/2013 | Young et al. |
| 8,444,638 B2 | 5/2013 | Woloszko et al. |
| 8,465,484 B2 | 6/2013 | Davalos et al. |
| 8,465,486 B2 | 6/2013 | Danek et al. |
| 8,588,886 B2 | 11/2013 | de la Rama et al. |
| 8,591,461 B2 | 11/2013 | Boatman |
| 8,617,158 B2 | 12/2013 | Garabedian et al. |
| 8,647,339 B2 | 2/2014 | Satake |
| 8,657,814 B2 | 2/2014 | Werneth et al. |
| 8,734,439 B2 | 5/2014 | Gough et al. |
| 8,814,855 B2 | 8/2014 | DiCarlo et al. |
| 8,834,461 B2 | 9/2014 | Werneth et al. |
| 8,979,838 B2 * | 3/2015 | Woloszko ............ A61B 18/042 606/34 |
| 8,979,841 B2 | 3/2015 | Kunis et al. |
| 9,078,665 B2 | 7/2015 | Moss et al. |
| 9,131,980 B2 | 9/2015 | Bloom |
| 9,839,472 B2 | 12/2017 | Rioux et al. |
| 9,848,936 B2 | 12/2017 | Rioux et al. |
| 9,855,098 B2 | 1/2018 | Rioux |
| 2001/0031941 A1 | 10/2001 | Edwards et al. |
| 2002/0026186 A1 | 2/2002 | Woloszko et al. |
| 2002/0062123 A1 | 5/2002 | McClurken et al. |
| 2002/0087208 A1 | 7/2002 | Koblish et al. |
| 2002/0095152 A1 * | 7/2002 | Ciarrocca .......... A61B 18/1402 606/48 |
| 2002/0115992 A1 | 8/2002 | Utley et al. |
| 2002/0120259 A1 * | 8/2002 | Lettice ................ A61B 18/148 606/32 |
| 2002/0120267 A1 | 8/2002 | Phan |
| 2002/0128641 A1 | 9/2002 | Underwood et al. |
| 2003/0009166 A1 | 1/2003 | Moutafis et al. |
| 2003/0036680 A1 | 2/2003 | Black |
| 2003/0130711 A1 | 7/2003 | Pearson et al. |
| 2003/0216725 A1 | 11/2003 | Woloszko et al. |
| 2003/0225403 A1 | 12/2003 | Woloszko et al. |
| 2004/0087936 A1 | 5/2004 | Stern et al. |
| 2004/0092960 A1 | 5/2004 | Abrams et al. |
| 2005/0049454 A1 * | 3/2005 | Ouchi ................ A61B 18/1492 600/105 |
| 2005/0070894 A1 | 3/2005 | McClurken |
| 2005/0154386 A1 | 7/2005 | West et al. |
| 2005/0187491 A1 * | 8/2005 | Burbank ................ A61B 18/14 600/564 |
| 2006/0212032 A1 | 9/2006 | Daniel et al. |
| 2006/0259027 A1 * | 11/2006 | Kwan ................ A61B 18/1477 606/41 |
| 2007/0083195 A1 | 4/2007 | Werneth et al. |
| 2008/0004534 A1 | 1/2008 | Gelbart et al. |
| 2008/0015565 A1 * | 1/2008 | Davison ............ A61B 18/1206 606/37 |
| 2008/0103494 A1 | 5/2008 | Rioux et al. |
| 2008/0140001 A1 | 6/2008 | Globerman et al. |
| 2008/0234673 A1 * | 9/2008 | Marion .............. A61B 18/1482 606/45 |
| 2009/0171340 A1 * | 7/2009 | Young ................ A61B 18/1477 606/33 |
| 2009/0248021 A1 | 10/2009 | McKenna |
| 2009/0292177 A1 | 11/2009 | Eggers et al. |
| 2009/0299355 A1 | 12/2009 | Bencini et al. |
| 2010/0114087 A1 | 5/2010 | Edwards et al. |
| 2010/0256629 A1 | 10/2010 | Wylie et al. |
| 2010/0292689 A1 | 11/2010 | Davison et al. |
| 2011/0172485 A1 | 7/2011 | Lubock |
| 2011/0257646 A1 | 10/2011 | Utley et al. |
| 2012/0029510 A1 | 2/2012 | Haverkost |
| 2012/0059437 A1 | 3/2012 | Shalev |
| 2012/0109250 A1 | 5/2012 | Cates et al. |
| 2012/0172680 A1 | 7/2012 | Gelfand et al. |
| 2013/0085493 A1 | 4/2013 | Bloom et al. |
| 2013/0158536 A1 * | 6/2013 | Bloom ................ A61B 18/1492 606/33 |
| 2013/0172870 A1 | 7/2013 | Germain et al. |
| 2013/0184702 A1 | 7/2013 | Neal, II et al. |
| 2013/0184706 A1 | 7/2013 | Gelbart et al. |
| 2013/0253506 A1 | 9/2013 | Rioux et al. |
| 2013/0310833 A1 * | 11/2013 | Brown ............... A61B 17/3476 606/45 |
| 2013/0338662 A1 * | 12/2013 | Weber .................... A61B 18/08 606/36 |
| 2014/0018788 A1 | 1/2014 | Engelman et al. |
| 2014/0018794 A1 | 1/2014 | Anderson et al. |
| 2014/0031810 A1 | 1/2014 | Mahvi et al. |
| 2014/0058376 A1 | 2/2014 | Horn et al. |
| 2014/0221998 A1 | 8/2014 | Latterell |
| 2014/0276731 A1 | 9/2014 | Voegele et al. |
| 2014/0276748 A1 * | 9/2014 | Ku ....................... A61B 18/18 606/33 |
| 2014/0378960 A1 * | 12/2014 | Fischer ............... A61B 5/0075 606/34 |
| 2015/0018817 A1 | 1/2015 | Willard |
| 2015/0141982 A1 * | 5/2015 | Lee ..................... A61B 5/6858 606/41 |
| 2016/0113707 A1 | 4/2016 | Sahakian et al. |
| 2016/0113708 A1 | 4/2016 | Moss et al. |
| 2016/0184008 A1 | 6/2016 | Papaioannou et al. |
| 2016/0317221 A1 | 11/2016 | Rioux |
| 2017/0000559 A1 | 1/2017 | Rioux et al. |
| 2017/0027633 A1 | 2/2017 | Wham et al. |
| 2017/0119454 A1 | 5/2017 | Rioux et al. |
| 2017/0172646 A1 * | 6/2017 | Patel .................. A61B 18/1206 |
| 2017/0215947 A1 | 8/2017 | Rioux et al. |
| 2017/0215951 A1 | 8/2017 | Wang et al. |
| 2017/0281267 A1 | 10/2017 | Rioux et al. |
| 2017/0281271 A1 | 10/2017 | Rioux |
| 2018/0014880 A1 | 1/2018 | Rioux et al. |
| 2018/0078305 A1 | 3/2018 | Rioux et al. |
| 2018/0104004 A1 | 4/2018 | Rioux et al. |

FOREIGN PATENT DOCUMENTS

| | | |
|---|---|---|
| DE | 102010032932 A1 | 2/2012 |
| EP | 0777445 B1 | 6/1999 |
| EP | 2942023 A3 | 2/2016 |
| EP | 3040043 B1 | 1/2018 |
| JP | 3009735 B2 | 2/2000 |
| WO | 9510326 A1 | 4/1995 |
| WO | 9942047 A1 | 8/1999 |
| WO | 0051683 A1 | 9/2000 |
| WO | 2007103986 A2 | 9/2007 |
| WO | 2011143468 A2 | 11/2011 |
| WO | 2012015722 A1 | 2/2012 |
| WO | 2012050637 A1 | 4/2012 |
| WO | 2014022379 A1 | 2/2014 |
| WO | 2014189887 A2 | 11/2014 |
| WO | 2015/142674 A1 | 9/2015 |
| WO | 2015163846 A1 | 10/2015 |
| WO | 2015200518 A1 | 12/2015 |
| WO | 2016181318 A1 | 11/2016 |

OTHER PUBLICATIONS

Extended European Search Report dated Jun. 10, 2016 for European Application No. 13825361.2 (13 Pages).

International Search Report and Written Opinion of the International Searching Authority dated May 16, 2017 for International Application No. PCT/US2017/015582 (11 pages).

International Search Report and Written Opinion of the International Searching Authority dated Aug. 22, 2016 for International Application No. PCT/US2016/030081 (11 Pages).

International Search Report and Written Opinion of the International Searching Authority dated Aug. 5, 2015 for International Application No. PCT/US2015/020596 (13 Pages).

International Search Report and Written Opinion of the International Searching Authority dated Nov. 29, 2013 or International Application No. PCT/US2013/052703 (11 Pages).

International Search Report and Written Opinion of the International Searching Authority dated Feb. 2, 2017 for International Application No. PCT/US2016/059345 (10 Pages).

(56) References Cited

OTHER PUBLICATIONS

International Search Report and Written Opinion of the International Searching Authority dated May 16, 2017 for International Application No. PCT/US2017/015584 (11 pages).
"Aquamantys System" Product Brochure, Medtronic, 2014 (12 Pages).
"Starburst Talon" Specifications Brochure, Angiodynamics, 2013 (2 Pages).
Medtronic, "Aquamantys Bipolar Sealers." Electrosurgical Products, Jun. 2017. Retrieved Jul. 21, 2017. <http://www.medtronic.com/us-en/healthcare-professionals/products/general-surgery/electrosurgical/aquamantys-bipolar-sealers.html> (11 Pages).
International Search Report and Written Opinion of the International Searching Authority dated Nov. 1, 2018 for International Application No. PCT/US2018/043654 (10 Pages).
International Search Report and Written Opinion of the International Searching Authority dated Nov. 15, 2018 for International Application PCT/US2018/043658 (15 Pages).
Notice of Allowance dated Jul. 24, 2018 for U.S. Appl. No. 15/784,778 (12 Pages).
International Search Report and Written Opinion of the International Searching Authority dated Aug. 26, 2018 for International Application No. PCT/US2017/059850 (10 Pages).
International Search Report and Written Opinion of the Interational Searching Authority dated Feb. 27, 2018 for International Application No. PCT/US2017/056754 (11 Pages).
Non-Final Office Action dated May 7, 2018 for U.S. Appl. No. 15/142,616 (13 Pages).
International Search Report and Written Opinion dated Jun. 6, 2018 for International Application No. PCT/US2018/019151 (17 Pages).
International Search Report and Written Opinion of the International Searching Authority dated Sep. 16, 2018 for International Application No. PCT/US2018/036268 (11 Pages).
International Search Report and Written Opinion of the International Searching Authority dated Jun. 11, 2017 for International Application No. PCT/US2017/019398 (27 Pages).
Non-Final Office Action dated Aug. 11, 2017 for U.S. Appl. No. 15/337,334 (11 Pages).
Response to Non-Final Office Action Filed Sep. 20, 2017 for U.S. Appl. No. 15/337,334 (6 Pages).
Non-Final Office Action dated Aug. 11, 2017 for U.S. Appl. No. 15/624,327 (11 Pages).
Response to Non-Final Office Action Filed Sep. 19, 2017 for U.S. Appl. No. 15/624,327 (8 Pages).
Non-Final Office Action dated Aug. 4, 2017 for U.S. Appl. No. 15/624,230 (18 Pages).
Response to Non-Final Office Action Filed Sep. 20, 2017 for U.S. Appl. No. 15/624,230 (10 Pages).
Extended European Search Report issued in European Application No. 16787228.2, dated Nov. 27, 2018, 6 pages.
Extended European Search Report issued in European Application No. 16860886.7, dated Jun. 12, 2019, 8 pages.
Extended European Search Report issued in European Application No. 17747970.6, dated Jul. 16, 2019, 6 pages.
Extended European Search Report issued in European Application No. 17828289.3, dated Feb. 6, 2020, 5 pages.
Extended European Search Report issued in European Application No. 17895158.8, dated Feb. 28, 2020, 8 pages.
Extended European Search Report issued in European Application No. 19219030.4, dated Jun. 26, 2020, 6 pages.
Official Action issued in Japanese Patent Application No. 2018-540040, dated Jun. 19, 2019, 11 pages.

* cited by examiner

RESECTING AND COAGULATING TISSUE

CROSS-REFERENCE TO RELATED APPLICATIONS

This application claims the benefit of, and priority to, U.S. Provisional Application No. 62/301,907, filed Mar. 1, 2016, the content of which is hereby incorporated by reference herein in its entirety.

FIELD

The present disclosure relates generally to medical devices, and, more particularly, to an ablation device configured to achieve simultaneous resection and coagulation, or hemostatic sealing, of a tissue.

BACKGROUND

There are many medical procedures in which tissue is cut or carved away for diagnostic or therapeutic reasons. For example, during hepatic transection, one or more lobes of a liver containing abnormal tissue, such as malignant tissue or fibrous tissue caused by cirrhosis, are cut away. There are a number of available electrosurgical devices for carrying out resection of tissue. However, regardless of the electrosurgical device used, extensive bleeding can occur, which can obstruct the surgeon's view and lead to dangerous blood loss levels, requiring transfusion of blood, which increases the complexity, time, and expense of the resection procedure.

In order to prevent extensive bleeding or accumulation of fluid, hemostatic mechanisms, such as blood inflow occlusion, coagulants, as well as energy coagulation (e.g., electrosurgical coagulation or argon-beam coagulation) can be used. Unlike resection, which involves application of highly intense and localized heating sufficient enough to break intercellular bonds, energy coagulation of tissue involves the application of low level current that denatures cells to a sufficient depth without breaking intercellular bonds, i.e., without cutting the tissue.

Because of their natural coagulation capability, ease of use, and ubiquity, electrosurgical modalities may be used to resect tissue. However, when electrosurgically resecting tissue, care must be taken to prevent the heat generated by the electrode from charring the tissue, which generates an undesirable odor, results in tissue becoming stuck on the electrosurgical probe, and most importantly, increases tissue resistance, thereby reducing the efficiency of the procedure. Current electrosurgical modalities, however, may generally lack the ability to be selectively and efficiently operated in a resecting mode and a coagulation mode, or both, so as to effectively resect tissue, while preventing tissue charring and maintaining hemostasis at the treatment site.

SUMMARY

The present invention relates to an ablation device configured to achieve both resection and coagulation of tissue. The ablation device can be used during an electrosurgical resection procedure to both resect tissue and further selectively coagulate surrounding tissue in the resection site so as to prevent or stop fluid accumulation (e.g., blood from vessel(s)) as a result of the resection of tissue. Accordingly, the ablation device of the present invention may be particularly useful in procedures involving the removal of unhealthy, or otherwise undesired, tissue from any part of the body in which resection may be beneficial. Thus, tumors, both benign and malignant, may be removed via surgical intervention with an ablation device described herein.

The tissue ablation device of the present invention generally includes a probe including an elongated shaft configured as a handle and adapted for manual manipulation and a nonconductive distal portion, or distal tip, coupled to the shaft. The nonconductive distal tip includes an electrode array configured to operate in a coagulation mode. The electrode array is composed of a plurality of conductive wires, wherein one or more of the wires may receive energy in the form of electrical current from a source (e.g., RF generator) and emit RF energy in response, resulting in coagulation of tissue in contact therewith. The nonconductive distal tip further includes a single cutting, or resecting, conductive wire. The cutting wire is configured to receive energy in the form of electrical current from the source (e.g., RF generator) and emit RF energy in response, thereby resulting in the resection of a tissue. The device may include a device controller, for example, configured to selectively control the supply of electrical current to the coagulation electrode array and the cutting wire, thereby allowing the device to operate in a cutting mode, a coagulation mode, or both such that the device can simultaneously resect and coagulate tissue at the target site.

The ability of the device to provide both resection and coagulation of tissue is dependent, not only on the nature of the electrical energy delivered to the conductive wires of the electrode array or the single cutting wire, but also on the geometry of the conductive wires along the nonconductive tip. The smaller the surface area of an electrode in proximity to the tissue, the greater the current density of an electrical arc generated by the electrode, and thus the more intense the thermal effect, thereby cutting the tissue. In contrast, the greater the surface area of the electrode in proximity to the tissue, the less the current density of the electrical arc generated by the electrode, thereby coagulating the tissue.

As such, the distal tip has a specific geometry that plays an important role in determining the current density (i.e., the amount of current distributed over an area) of energy emitted by the electrode array and cutting wire. In particular, the distal tip includes at least two opposing sides or faces sharing a common distal-facing edge. Each of the opposing sides of the distal tip includes a generally planar surface providing a relatively large surface area upon which the electrode array is positioned. The distal-facing edge has a leading end and a trailing end, wherein the leading end extends further from the distal tip than the trailing end. The cutting wire is positioned along, and generally follows the length of, the distal-facing edge. Accordingly, a portion of the cutting wire adjacent to the leading end of the edge has a relatively small surface area (when compared to the electrode array surface area) forming an energy focusing portion. Thus, because of the arrangement of the cutting wire along the distal-facing edge, including the energy-focusing portion at the leading end of the edge, the cutting wire can be placed in proximity to the tissue and cut the tissue. In contrast, positioning of the coagulation electrode array on the relatively large surface area of the planar sides or faces of the distal tip allows the electrode array to coagulate tissue.

The ablation device of the present invention is further configured to provide a conductive fluid, such as saline, to the distal tip, which may include one or more ports (e.g., ports through which conductive wires are threaded, additional fluid ports, etc.). The saline weeping through the ports and to an outer surface of the distal tip is able to carry electrical current from electrode array and/or the cutting wire, such that energy is transmitted from the electrode array, or cutting wire, to the tissue by way of the saline weeping from the ports, thereby creating a virtual electrode. Accordingly, upon the fluid weeping through the ports, a pool or thin film of fluid is formed on the exterior surface of the distal tip and is configured to resect and/or coagulate surrounding tissue via the electrical current carried from the electrode array.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

Figure 1:
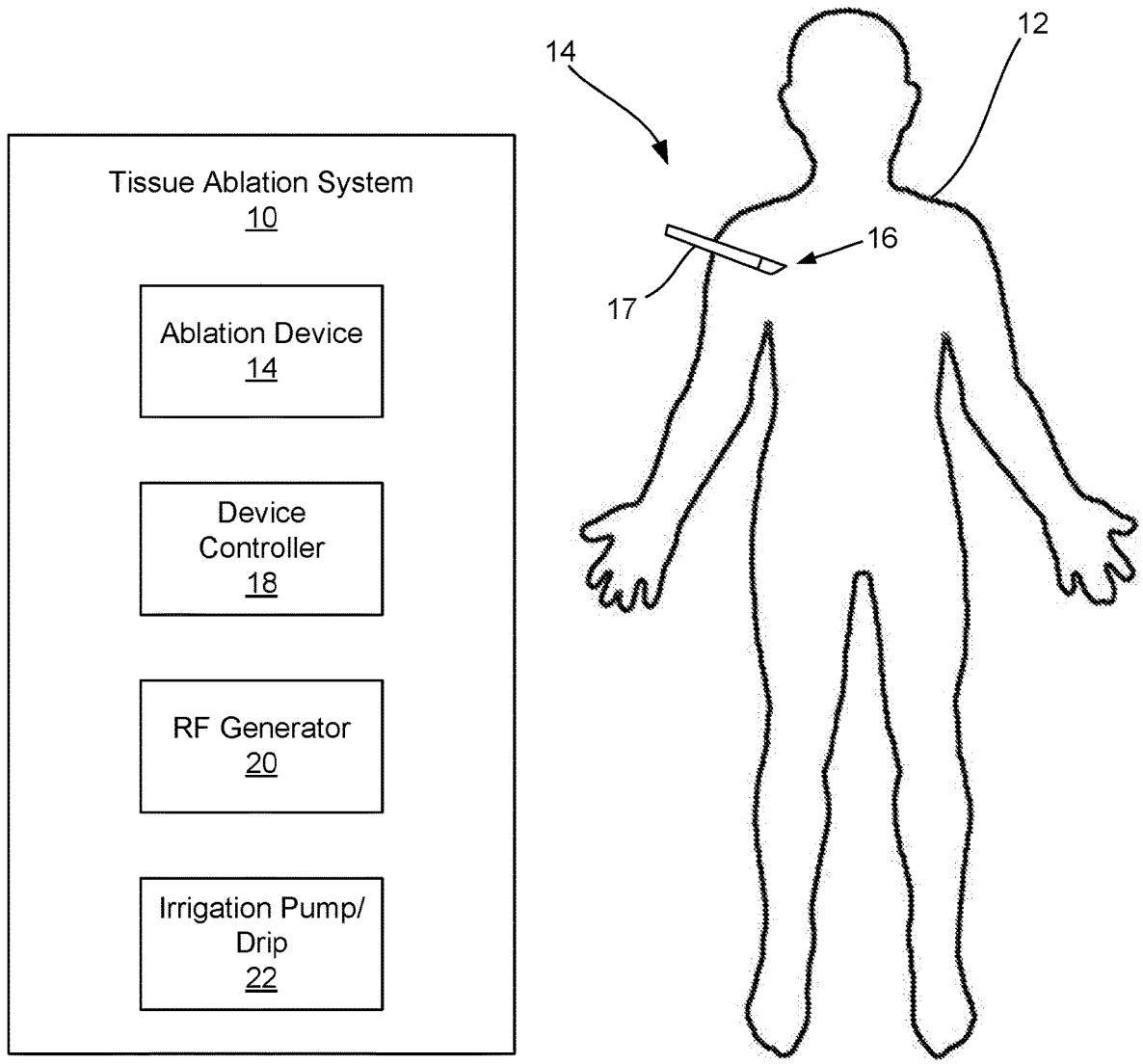
FIG. 1 is a schematic illustration of an ablation system consistent with the present disclosure.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

By way of overview, the present disclosure is generally directed to a tissue ablation system including an ablation device to be delivered to a target site and achieve both resection and coagulation of tissue. The ablation device can be used during an electrosurgical resection procedure to both resect tissue and further selectively coagulate surrounding tissue in the resection site so as to prevent or stop fluid accumulation (e.g., blood from vessel(s)) as a result of the resection of tissue. Accordingly, the ablation device of the present invention may be particularly useful in procedures involving the removal of unhealthy, or otherwise undesired, tissue from any part of the body in which resection may be beneficial. Thus, tumors, both benign and malignant, may be removed via surgical intervention with an ablation device described herein.

The tissue ablation device of the present invention generally includes a probe including an elongated shaft configured as a handle and adapted for manual manipulation and a nonconductive distal portion (also referred to herein as "distal tip") coupled to the shaft. The nonconductive distal tip includes an electrode array configured to operate in a coagulation mode. The electrode array is composed of a plurality of conductive wires, wherein one or more of the wires may receive energy in the form of electrical current from a source (e.g., RF generator) and emit RF energy in response, resulting in coagulation of tissue in contact therewith. The nonconductive distal tip further includes a single cutting, or resecting, conductive wire. The cutting wire is configured to receive energy in the form of electrical current from the source (e.g., RF generator) and emit RF energy in response, thereby resulting in the resection of a tissue. The device may include a device controller, for example, configured to selectively control the supply of electrical current to the coagulation electrode array and the cutting wire, thereby allowing the device to operate in a cutting mode, a coagulation mode, or both such that the device can simultaneously resect and coagulate tissue at the target site.

The ability of the device to provide both resection and coagulation of tissue is dependent, not only on the nature of the electrical energy delivered to the conductive wires of the electrode array or the single cutting wire, but also on the geometry of the conductive wires along the nonconductive tip. The smaller the surface area of an electrode in proximity to the tissue, the greater the current density of an electrical arc generated by the electrode, and thus the more intense the thermal effect, thereby cutting the tissue. In contrast, the greater the surface area of the electrode in proximity to the tissue, the less the current density of the electrical arc generated by the electrode, thereby coagulating the tissue.

As such, the distal tip has a specific geometry that plays an important role in determining the current density (i.e., the amount of current distributed over an area) of energy emitted by the electrode array and cutting wire. In particular, the distal tip includes at least two opposing sides or faces sharing a common distal-facing edge. Each of the opposing sides of the distal tip includes a generally planar surface providing a relatively large surface area upon which the electrode array is positioned. The distal-facing edge has a leading end and a trailing end, wherein the leading end extends further from the distal tip than the trailing end. The cutting wire is positioned along, and generally follows the length of, the distal-facing edge. Accordingly, a portion of the cutting wire adjacent to the leading end of the edge has a relatively small surface area (when compared to the electrode array surface area) forming an energy focusing portion. Thus, because of the arrangement of the cutting wire along the distal-facing edge, including the energy-focusing portion at the leading end of the edge, the cutting wire can be placed in proximity to the tissue and cut the tissue. In contrast, positioning of the coagulation electrode array on the relatively large surface area of the planar sides or faces of the distal tip allows the electrode array to coagulate tissue.

The ablation device of the present invention is further configured to provide a conductive fluid, such as saline, to the distal tip, which may include one or more ports (e.g., ports through which conductive wires are threaded, additional fluid ports, etc.). The saline weeping through the ports and to an outer surface of the distal tip is able to carry electrical current from electrode array and/or the cutting wire, such that energy is transmitted from the electrode array, or cutting wire, to the tissue by way of the saline weeping from the ports, thereby creating a virtual electrode. Accordingly, upon the fluid weeping through the ports, a pool or thin film of fluid is formed on the exterior surface of the distal tip and is configured to resect and/or coagulate surrounding tissue via the electrical current carried from the electrode array.

The devices and systems of the present disclosure can help to ensure that target tissue can be removed via resection while further providing a coagulation capability for addressing any fluid accumulation issues or extensive bleeding as a result of the resection, thereby improving a surgeon's ability to carry out the resection procedure. For example, when a blood vessel is encountered, RF energy can be applied via the electrode array operating in the coagulation mode, so as to shrink the collagen in the blood vessel, thereby closing the blood lumen and achieving hemostasis. In some instances, the cutting wire may be used to hemostatically seal smaller blood vessels (e.g., less than 3 mm in diameter). For example, hemostasis may be achieved via the cutting wire, for example, by utilizing the energy-focusing point in contact with the blood vessel. During or after resection of the tissue, RF energy can be applied to any "bleeders" (i.e., vessels from which blood flows or oozes) to provide complete hemostasis for the resected organ.

FIG. 1 is a schematic illustration of an ablation system 10 for providing improved resection and coagulation of tissue during a resection procedure in a patient 12. The ablation system 10 generally includes an ablation device 14, which includes a probe having a distal tip or portion 16 and an elongated catheter shaft 17 to which the distal tip 16 is connected. The catheter shaft 17 may generally include a nonconductive elongated member including a fluid delivery lumen. The ablation device 14 may further be coupled to a device controller 18 and an ablation generator 20 over an electrical connection (electrical line 32 shown in FIG. 2), and an irrigation pump or drip 22 over a fluid connection (fluid line 36 shown in FIG. 2).

The device controller 18 may include hardware/software configured to provide a user with the ability to control electrical output to the ablation device 14 in a manner so as to control the resection or coagulation of tissue. For example, as will be described in greater detail herein, the ablation device may be configured to operate in a "cutting mode", a "coagulation mode", or both modes simultaneously depending on input from a user. In some embodiments, the ablation device may be configured to operate in other modes, in addition to the "cutting" and "coagulation" modes. For example, in some embodiments, the device may be configured to operate in a "measurement mode" in which data can be collected, such as certain measurements (e.g., temperature, conductivity (impedance), etc.) can be taken and further used by the controller 18 so as to provide an estimation of the state of tissue during a electrosurgical resection procedure, as will be described in greater detail herein.

Further still, the device controller 18 may include a custom ablation shaping (CAS) system configured to provide a user with custom ablation shaping, which includes the creation of custom, user-defined ablation geometries or profiles from the ablation device 14. The CAS system may further be configured to provide ablation status mapping based on real-time data collection (e.g., measurements) collected by the device, wherein such a CAS system is described in co-pending U.S. application Ser. No. 15/419,269, filed Jan. 30, 2017, the entirety of which is incorporated by reference herein. In some cases, the device controller 18 may be housed within the ablation device 14. The ablation generator 20 may also connected to a return electrode that is attached to the skin of the patient 12.

As will be described in greater detail herein, during a resection procedure, the ablation generator 20 may generally provide RF energy (e.g., electrical energy in the radiofrequency (RF) range (e.g., 350-800 kHz)) to an electrode array of the ablation device 14, as controlled by the device controller 18. At the same time, saline may also be released from the distal tip 16. The RF energy travels through the blood and tissue of the patient 12 to the return electrode and, in the process, ablates the region(s) of tissues adjacent to portions of the electrode array that have been activated.

Figure 2:
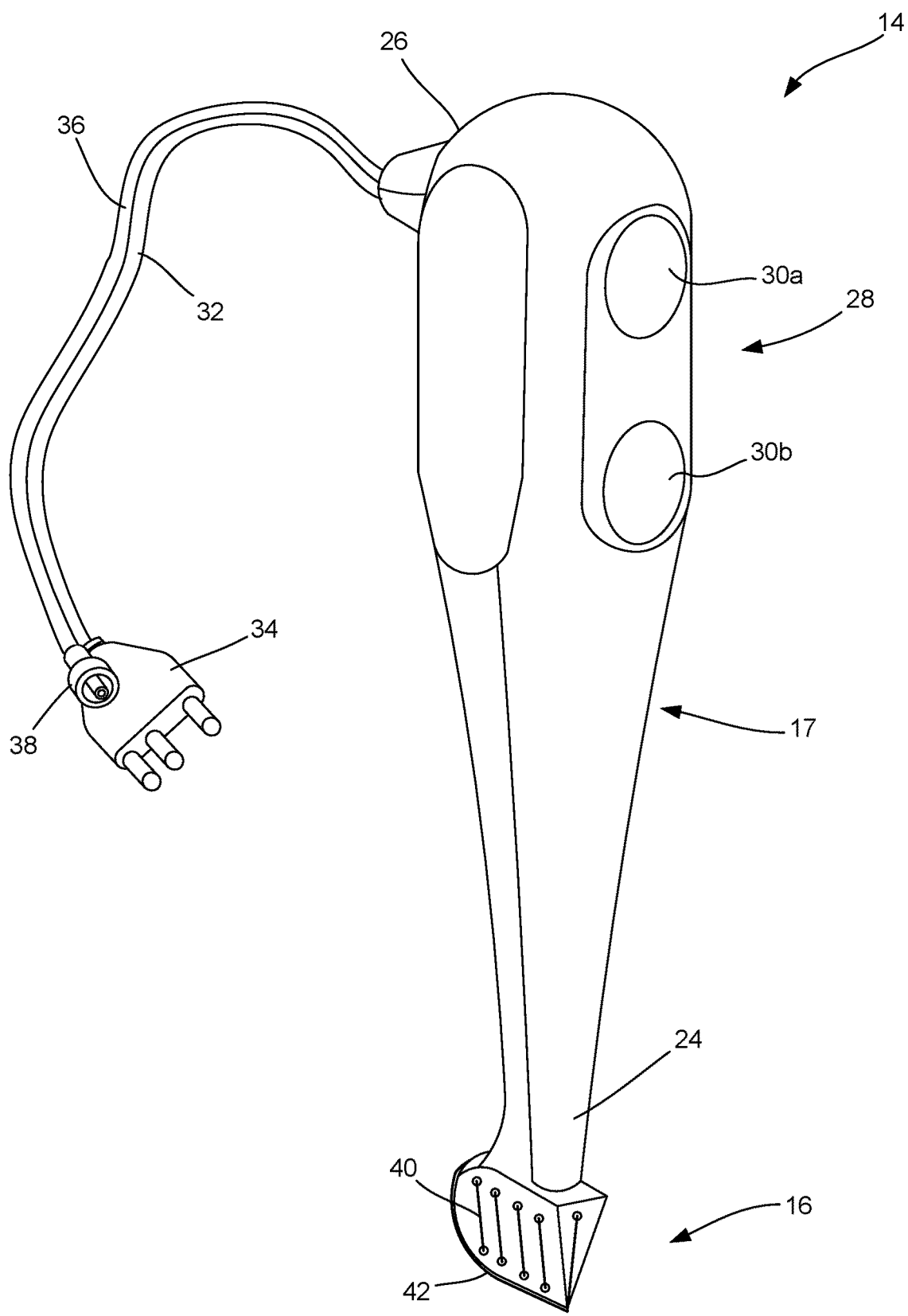
FIG. 2 is a perspective view of one embodiment of an ablation device compatible with the ablation system of FIG. 1.

FIG. 2 is a perspective view of ablation device 14. As previously described, the ablation device 14 includes a probe 17 including an elongated shaft configured as a handle and adapted for manual manipulation. Accordingly, as shown in FIG. 2, the probe 17 is in the form of a handle having a distal end 24 to which the distal tip 16 is coupled and a proximal end 26. As shown, the proximal end 26 of the probe 17 may be coupled to the ablation generator 20 and/or irrigation pump 22 via an electrical line 32 and a fluid line 36, respectively. Each of the electrical line 32 and fluid line 36 may include an adaptor end 34, 38 configured to couple the associated lines with a respective interface on the ablation generator 20 and irrigation pump 22.

In some examples, the ablation device 14 may further include a user interface 28 serving as the device controller 18 and in electrical communication with the ablation generator 20 and the ablation device 14. The user interface 28 may include, for example, selectable buttons 30a, 30b for providing a user with one or more operating modes with respect to controlling the resection and coagulation output of the device 14, as will be described in greater detail herein. For example, the selectable buttons 30a, 30b allow a user to control electrical output to the ablation device 14 in a manner so as to control the resection or coagulation of tissue, such that selection of button 30a results in a cutting mode (e.g., energizing cutting wire) and selection of button 30b results in a coagulation mode (energizing electrode array).

The nonconductive distal tip includes an electrode array 40 configured to operate in a coagulation mode and a single and separate cutting, or resecting, conductive wire 42 configured to operate in a cutting mode. The electrode array 40 is generally composed of a plurality of conductive wires (shown as four separate conductive wires), wherein one or more of the wires may receive energy in the form of electrical current from the RF generator 20 and emit RF energy in response, resulting in coagulation of tissue in contact therewith. The cutting wire 42 is configured to receive energy in the form of electrical current from the source (e.g., RF generator) and emit RF energy in response, thereby resulting in the resection of a tissue. As previously described, a user need only provide input (e.g., select one of buttons 30a, 30b) so as to operate the ablation device 14 in the cutting mode, coagulation mode, or both, in which a supply of electrical current is provided to the cutting wire 42 or one or more of the conductive wires of the coagulation electrode array 40, or both.

The distal tip 16 may include a non-conductive material (e.g., a polyamide) as a layer on at least a portion of an internal surface, an external surface, or both an external and internal surface. In other examples, the tip 16 may be formed from a non-conductive material. Additionally or alternatively, the tip 16 material can include an elastomeric material or a shape memory material. In some embodiments, the tip 16 may be rigid, and thus may maintain a default shape.

The distal tip 16 includes a specific geometry or shape that plays an important role in determining the current density (i.e., the amount of current distributed over an area) of energy emitted by the electrode array 40 and cutting wire 42. The ability of the device 14 to provide both resection and coagulation of tissue is dependent, not only on the nature of the electrical energy delivered to the conductive wires of the electrode array 40 or the single cutting wire 42, but also on the geometry of the conductive wires along the tip 16. The smaller the surface area of an electrode in proximity to the tissue, the greater the current density of an electrical arc generated by the electrode, and thus the more intense the thermal effect, thereby cutting the tissue. In contrast, the greater the surface area of the electrode in proximity to the tissue, the less the current density of the electrical arc generated by the electrode, thereby coagulating the tissue.

Figure 3A:
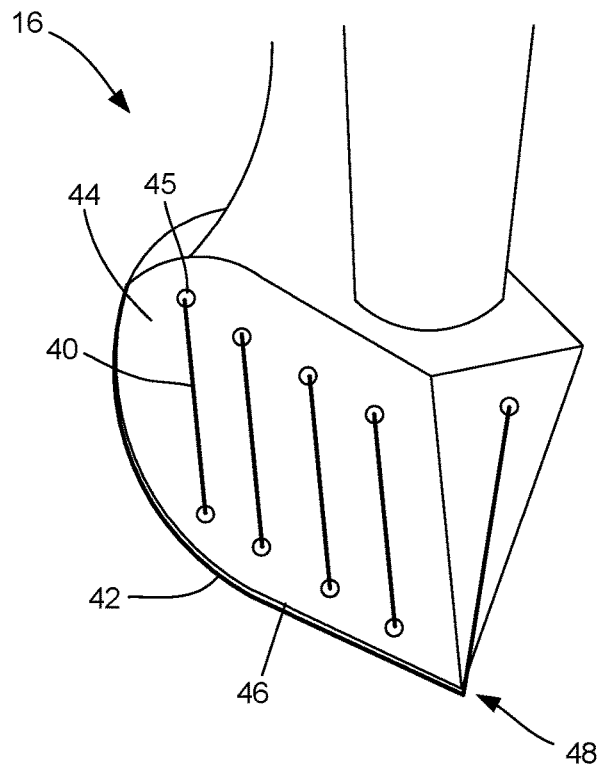
FIGS. 3A, 3B, 3C, and 3D are perspective and side views of the nonconductive distal tip of the ablation device of FIG. 2 in greater detail.

FIGS. 3A, 3B, 3C, and 3D are various views of the nonconductive distal tip 16 of the ablation device 14 in greater detail. FIG. 3A shows a perspective view of the distal tip 16. As shown, the distal tip 16 generally includes at least two opposing sides or faces 44 (44a, 44b in FIG. 3C) sharing a common distal-facing edge 46. Each of the opposing sides 44 of the distal tip 16 includes a generally planar surface providing a relatively large surface area upon which the electrode array 40 is positioned. As illustrated in the figures, the electrode array includes at least four conductive wires, thus the electrode array 40 may include a plurality of conductive wires. It should be noted, however, that the electrode array 40 may include any number of conductive wires and is not limited to four or more. The plurality of conductive wires extend within the distal tip 16, through one or more ports 45 provided on the side 44 and along an external surface of the side 44. The conductive wires generally extend along the longitudinal length of the side 44 (in a vertical direction) and are spaced apart from each other. The conductive wires transmit RF energy from the ablation generator and can be formed of any suitable conductive material (e.g., a metal such as stainless steel, nitinol, or aluminum). In some examples, the conductive wires are metal wires.

It should be noted that other electrode array configurations are contemplated herein. For example, although shown to be arranged in a vertical fashion, the conductive wires of the electrode array 40 may be arranged in a different configuration. For example, in one embodiment, the conductive wires may be positioned substantially parallel to the distal-facing edge 46 or may be oriented at an angle relative to the distal-facing edge 46.

In some embodiments, one or more of the conductive wires can be electrically isolated from one or more of the remaining conductive wires, such that the electrical isolation enables various operation modes for the ablation device 14. For example, ablation energy may be supplied to one or more conductive wires in a bipolar mode, a unipolar mode, or a combination bipolar and unipolar mode. In the unipolar mode, ablation energy is delivered between one or more conductive wires of the electrode array 40 and a return electrode, for example. In bipolar mode, energy is delivered between at least two of the conductive wires, while at least one conductive wire remains neutral. In other words, at least, one conductive wire functions as a grounded conductive wire (e.g., electrode) by not delivering energy over at least one conductive wire.

Since each conductive wire in the electrode array 40 is electrically independent, each conductive wire can be connected in a fashion that allows for impedance measurements using bipolar impedance measurement circuits. For example, the conductive wires can be configured in such a fashion that tetrapolar or guarded tetrapolar electrode configurations can be used. For instance, one pair of conductive wires could function as the current driver and the current return, while another pair of conductive wires could function as a voltage measurement pair. Accordingly, a dispersive ground pad can function as current return and voltage references. Their placement dictate the current paths and thus having multiple references can also benefit by providing additional paths for determining the ablation status of the tissue. The impedance measurement capability of the device is described in co-pending U.S. application Ser. No. 15/337, 334, filed on Oct. 28, 2016 and U.S. application Ser. No. 15/419,269, filed Jan. 30, 2017, the entireties of which are incorporated by reference herein.

Figure 3B:
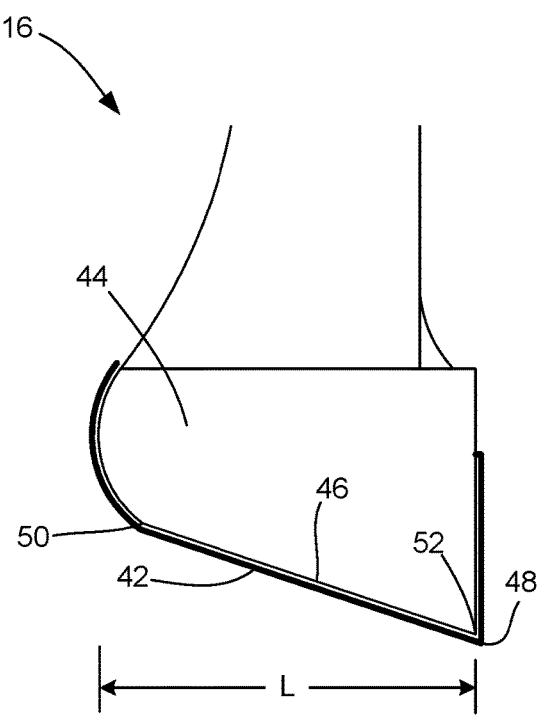
Figure 3C:
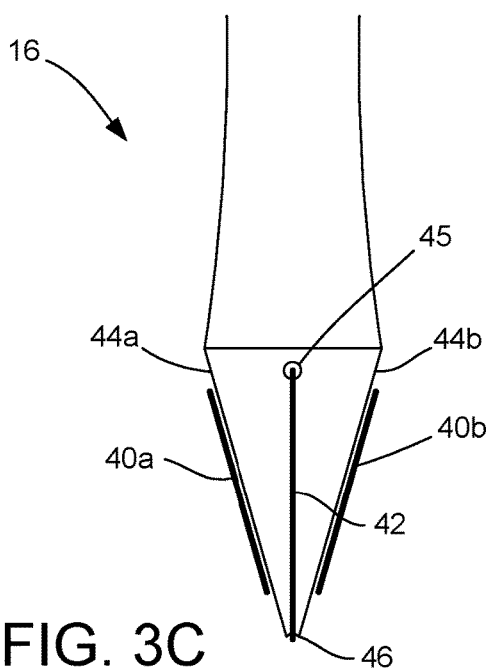
Figure 3D:
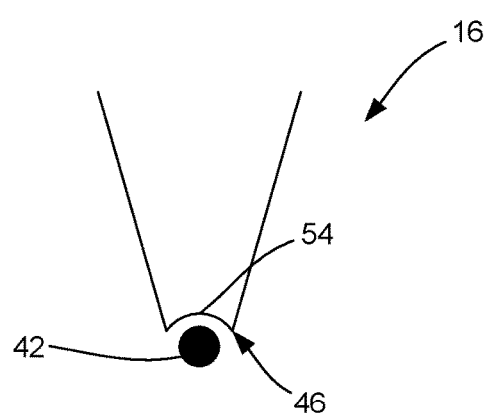

FIG. 3B is a side view of the distal tip 16 with the electrode array 40 removed so as to better illustrate a planar surface side 44 of the distal tip 16. As shown in FIG. 3B, the distal-facing edge 46 has a trailing end 50 and a leading end 52, wherein the leading end 52 extends further from the distal tip 16 than the trailing end 50. The cutting wire 42 is positioned along, and generally follows the length of, the distal-facing edge 46. The distal-facing edge 46 may have a length L between 0.5 cm to 5 cm, and, in some embodiments, the length L of the distal-facing edge 46 may be approximately 1 cm. In some embodiments, the distal-facing edge 46 may include a groove 54 formed along a length thereof and configured to receive and provide a guide along which the cutting wire 42 may sit (see FIG. 3D). Accordingly, a portion of the cutting wire 42 adjacent to the leading end 52 of the edge 46 has a relatively small surface area (when compared to the electrode array 40 surface area on side 44), thereby forming an energy focusing portion 48. Thus, because of the arrangement of the cutting wire 42 along the distal-facing edge 46, including the energy-focusing portion 48 at the leading end 52 of the edge 46, the cutting wire can be placed in proximity to the tissue and cut the tissue. In contrast, positioning of the coagulation electrode array 40 on the relatively large surface area of the planar sides or faces 44a, 44b of the distal tip 16 allows the electrode array to coagulate tissue.

Figure 4:
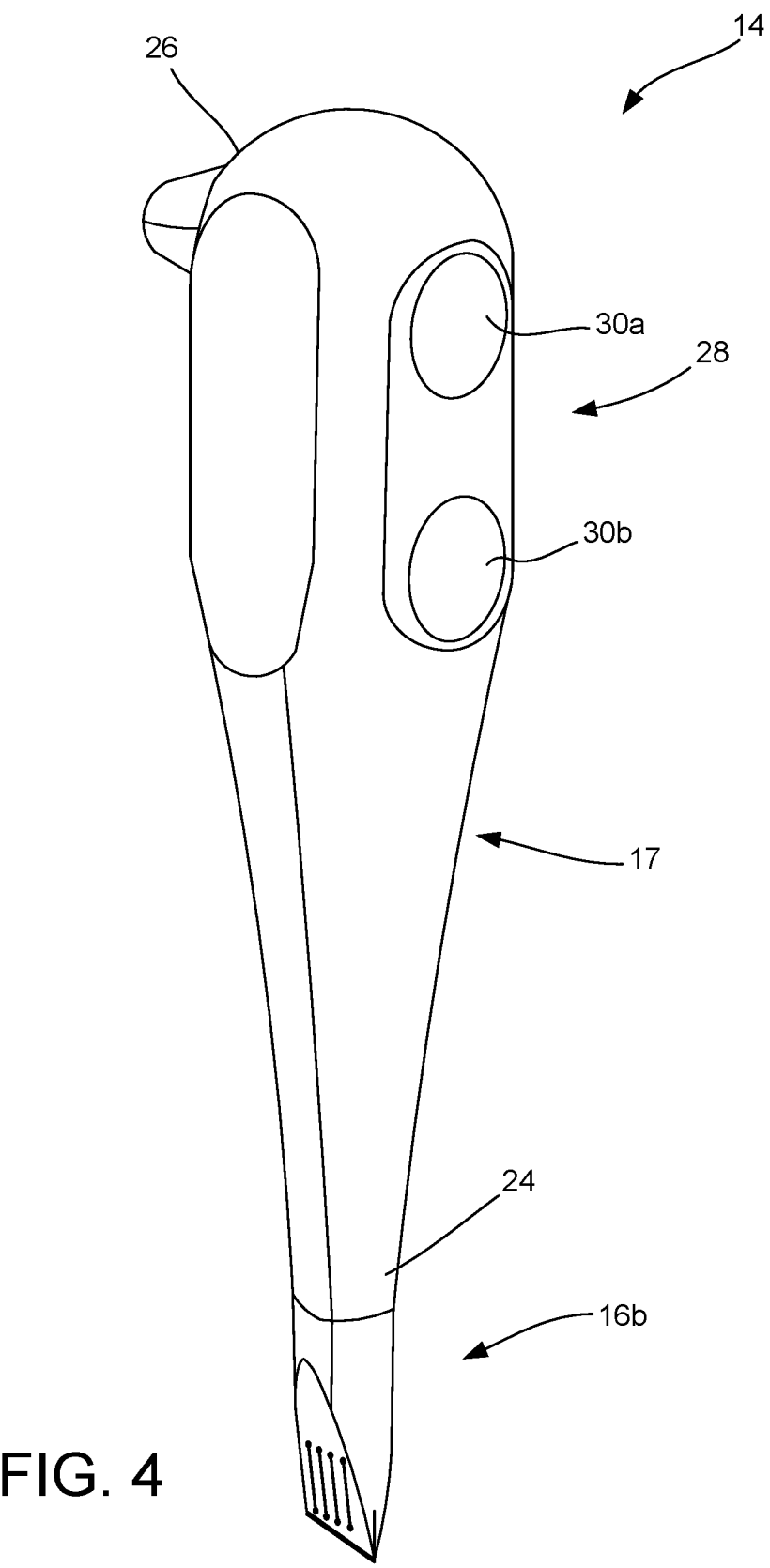
FIG. 4 is a perspective view of another embodiment of an ablation device compatible with the ablation system of FIG. 1.
Figure 5A:
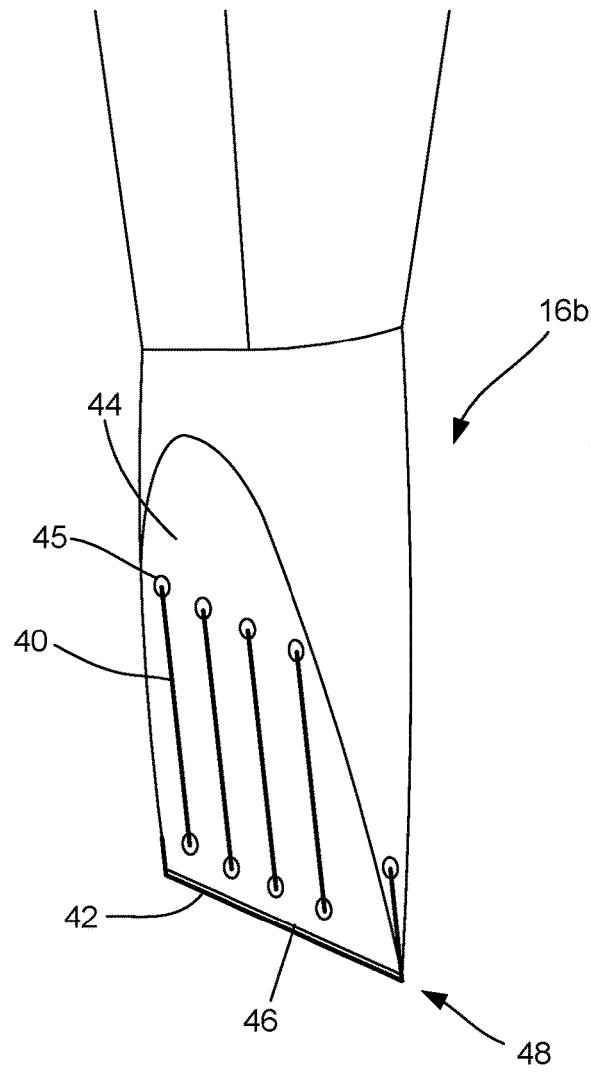
FIGS. 5A and 5B are perspective and side views of the nonconductive distal tip of the ablation device of FIG. 4 in greater detail.
Figure 5B:
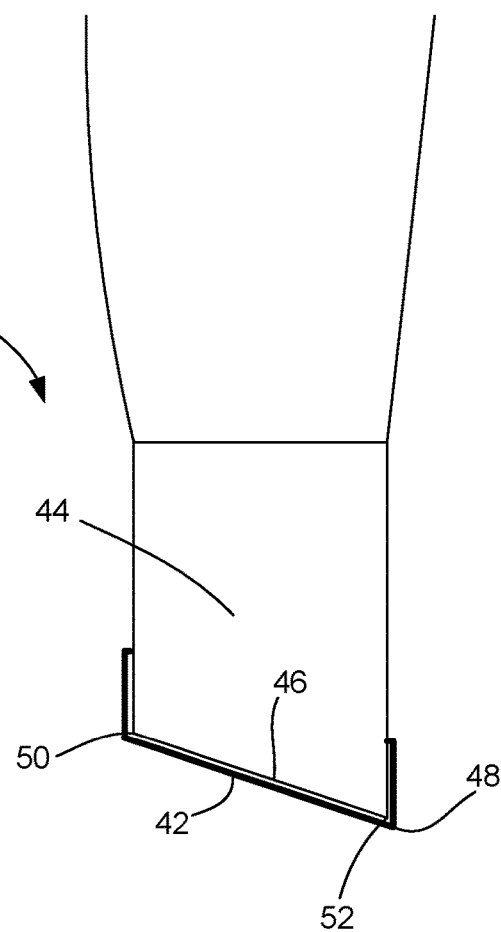

It should be noted that the ablation device 14 of the present disclosure may include different distal tip geometries or shapes. For example, FIG. 4 is a perspective view of another embodiment of a distal tip 16b for use with the ablation device 14 of the present invention. As shown, all elements of the ablation device 14 of FIG. 4 are identical to the ablation device 14 illustrated in FIG. 2, while the distal tip 16 has a different shape. FIGS. 5A and 5B are perspective and side views of the nonconductive distal tip 16b of the ablation device 14 of FIG. 4 in greater detail. In the embodiment shown in FIGS. 5A and 5B, the distal tip has a more squared-off shape, as opposed to the somewhat rounded off shape of distal tip 16 of FIGS. 2 and 3A-3D. In either case, the distal tip 16b has opposing sides 44 providing a substantially planar surface for the electrode array 40 and a distal-facing edge 46 for the cutting wire 42.

As previously described, the ablation device 14 of the present invention is further configured to provide a conductive fluid, such as saline, to the distal tip 16, which may include one or more ports 45 (e.g., ports through which conductive wires are threaded, additional fluid ports, etc.). The saline weeping through the ports 45 and to an outer surface of the distal tip 16 is able to carry electrical current from electrode array 40 and/or the cutting wire 42, such that energy is transmitted from the electrode array 40, or cutting wire 42, to the tissue by way of the saline weeping from the ports, thereby creating a virtual electrode. Accordingly, upon the fluid weeping through the ports, a pool or thin film of fluid is formed on the exterior surface of the distal tip 16 and is configured to resect and/or coagulate surrounding tissue via the electrical current carried from the electrode array.

As generally understood, the distal tip may be formed from two or more pieces configured to be coupled to one another to form the unitary distal tip 16, such as a configuration, including internal components and connections, as described in co-pending U.S. application Ser. No. 15/337, 334, filed on Oct. 28, 2016 and U.S. application Ser. No.

15/419,269, filed Jan. 30, 2017, the entireties of which are incorporated by reference herein, the entireties of which are incorporated by reference.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

As used in any embodiment herein, the term "controller", "module", "subsystem", or the like, may refer to software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The controller or subsystem may, collectively or individually, be embodied as circuitry that forms part of a larger system, for example, an integrated circuit (IC), system on-chip (SoC), desktop computers, laptop computers, tablet computers, servers, smart phones, etc.

Any of the operations described herein may be implemented in a system that includes one or more storage mediums having stored thereon, individually or in combination, instructions that when executed by one or more processors perform the methods. Here, the processor may include, for example, a server CPU, a mobile device CPU, and/or other programmable circuitry.

Also, it is intended that operations described herein may be distributed across a plurality of physical devices, such as processing structures at more than one different physical location. The storage medium may include any type of tangible medium, for example, any type of disk including hard disks, floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, Solid State Disks (SSDs), magnetic or optical cards, or any type of media suitable for storing electronic instructions. Other embodiments may be implemented as software modules executed by a programmable control device. The storage medium may be non-transitory.

As described herein, various embodiments may be implemented using hardware elements, software elements, or any combination thereof. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

What is claimed is:

1. A device for selectively resecting and coagulating tissue, the device comprising:
   a probe comprising:
      a nonconductive elongated shaft including at least one lumen extending therethrough; and
      a nonconductive distal tip extending from the shaft and in fluid communication with the at least one lumen and configured to receive a fluid therefrom, the nonconductive distal tip having a plurality of ports configured to allow passage of the fluid to an external surface of the distal tip and at least two opposing sides, each of the at least two opposing sides defining a substantially planar surface, and a distal-facing edge along which the at least two opposing sides converge, the distal-facing edge having a leading end and a trailing end, wherein the leading end extends further from the nonconductive distal tip than the trailing end;
   an electrode array comprising a plurality of independent conductive wires, each positioned along the external surface of the planar surface of at least one of the at least two opposing sides of the nonconductive distal tip, wherein the plurality of ports comprises a plurality of proximal ports and a plurality of distal ports and each of the plurality of independent conductive wires passes through one of the proximal ports and through a corresponding one of the distal ports, wherein one or more of the plurality of independent conductive wires is configured to receive an electrical current and conduct energy to be carried by the fluid passing through one or more of the plurality of ports for coagulation of a target tissue; and
   a single conductive cutting wire independent from the electrode array, positioned and extending along an entire length of the distal-facing edge of the nonconductive distal tip, wherein the cutting wire passes through another one of the proximal ports, the cutting wire configured to receive an electrical current to cause activation of the cutting wire, and having an energy focusing portion adjacent the leading end of the distal-facing edge, the energy focusing portion having a relatively smaller surface area than the surface area of the electrode array and configured, upon receipt of the electrical current, to convey a focused amount of energy to be carried by the fluid passing through the another proximal port away from the nonconductive distal tip sufficient for at least one of resection and coagulation of the target tissue, the focused amount of energy being greater than an amount of energy conveyed to the tissue by the electrode array.

2. The device of claim 1, wherein, upon receipt of the electrical current, the energy focusing portion is configured to convey the focused amount of energy away from the nonconductive distal tip sufficient for resection of the target tissue, wherein the energy is RF energy.

3. The device of claim 1, wherein the distal-facing edge of the nonconductive distal tip comprises a groove formed along a length thereof and configured to receive and retain the cutting wire within.

4. The device of claim 1, wherein, upon receipt of the electrical current, at least one of the plurality of independent conductive wires of the electrode array is configured to convey energy away from the nonconductive distal tip sufficient for coagulation of the target tissue, wherein the energy is RF energy.

5. The device of claim 1, further comprising a controller configured to receive input to and selectively control supply of electrical current to the electrode array and the cutting wire and to receive input.

6. The device of claim 5, wherein the controller is configured to provide an operating mode upon receipt of input, wherein the operating mode is at least one of a coagulation operating mode and a resection operating mode.

7. The device of claim 6, wherein the controller is configured to provide a measurement mode in which at least one of the electrode array and the cutting wire is configured to serve a portion of a sensor assembly configured to measure impedance.

8. The device of claim 6, wherein, upon receipt of input selecting the coagulation operating mode, the controller is configured to selectively control the supply of electrical current to the electrode array.

9. The device of claim 6, wherein, upon receipt of input selecting the resection operating mode, the controller is configured to selectively control the supply of electrical current to the cutting wire.

10. The device of claim 6, wherein the controller is configured to control one or more parameters associated with the supply of electrical current to the electrode array and the cutting wire depending on the operating mode.

11. The device of claim 10, wherein the one or more parameters include at least one of a level of electrical current to be supplied, a length of time in which the electrical current is to be supplied, one or more intervals over which the electrical current is to be supplied, or a combination thereof.

12. The device of claim 1, wherein each of the plurality of distal ports corresponds to one of the plurality of proximal ports such that a wire passing through a set of corresponding distal and proximal ports has a length that extends along the external surface of the planar surface of at least one of the at least two opposing sides of the nonconductive distal tip.

13. The device of claim 12, wherein each of the plurality of independent conductive wires of the electrode array translates along at least one of the at least two opposing sides of the nonconductive distal tip in a direction substantially parallel with a longitudinal axis of the device.

14. The device of claim 1, wherein each of the plurality of independent conductive wires of the electrode array extends through a different one of the plurality of distal ports and each of the plurality of independent conductive wires of the electrode array extends through a different one of the plurality of proximal ports.

15. The device of claim 1, wherein the cutting wire is configured to conduct electrical current to be carried by the conductive fluid along the external surface of the nonconductive distal tip for at least one of coagulation and resection of the target tissue.

16. The device of claim 1, wherein the external surface of the nonconductive distal tip comprises at least one portion of surface texturing to enhance fluid distribution.

* * * * *